(12) United States Patent  (10) Patent No.: US 8,852,258 B2
Lubinski et al.  (45) Date of Patent: Oct. 7, 2014

(54) CATHETER ASSEMBLY WITH USER-ASSISTING HANDLE

(75) Inventors: Alexander Arthur Lubinski, Rocklin, CA (US); Eric W. Leopold, Redwood City, CA (US); Gerald Ray Martin, Redwood City, CA (US)

(73) Assignee: NovoStent Corporation, Mountain View, CA (US)

( * ) Notice: Subject to any disclaimer, the term of this patent is extended or adjusted under 35 U.S.C. 154(b) by 529 days.

(21) Appl. No.: 13/279,724

(22) Filed: Oct. 24, 2011

(65) Prior Publication Data

US 2013/0103130 A1 Apr. 25, 2013

(51) Int. Cl.
*A61F 2/06* (2013.01)
*A61F 2/966* (2013.01)
*A61F 2/95* (2013.01)

(52) U.S. Cl.
CPC ......... *A61F 2/966* (2013.01); *A61F 2250/0018* (2013.01); *A61F 2230/0091* (2013.01); *A61F 2002/9517* (2013.01); *A61F 2230/0019* (2013.01)
USPC .......... 623/1.11; 623/1.12; 623/1.23; 604/27; 604/48; 604/502; 604/507; 604/510; 604/134

(58) Field of Classification Search
USPC ........... 623/1.11, 1.12, 1.23; 604/27, 48, 134, 604/502, 507, 508, 510
See application file for complete search history.

(56) References Cited

U.S. PATENT DOCUMENTS

| 6,572,643 B1 | 6/2003 | Gharibadeh |
| 7,635,382 B2 | 12/2009 | Pryor |
| 8,002,815 B2 * | 8/2011 | Laroya et al. ................ 623/1.12 |
| 2006/0136035 A1 * | 6/2006 | Hermann et al. ............ 623/1.11 |
| 2006/0286145 A1 * | 12/2006 | Horan et al. .................. 424/426 |
| 2008/0221657 A1 | 9/2008 | Laroya et al. |
| 2009/0024137 A1 | 1/2009 | Chuter et al. |
| 2010/0004606 A1 | 1/2010 | Hansen et al. |
| 2010/0312129 A1 | 12/2010 | Schecter |

FOREIGN PATENT DOCUMENTS

| RU | 2078588 C1 | 5/1997 |
| WO | 9636298 A1 | 11/1996 |

OTHER PUBLICATIONS

Feb. 14, 2013 International Search Report, PCT/US12/61680 6 pp.

\* cited by examiner

*Primary Examiner* — Victor Nguyen
*Assistant Examiner* — Kevin Everage
(74) *Attorney, Agent, or Firm* — James F. Hann; Haynes Beffel & Wolfeld LLP

(57) ABSTRACT

A catheter assembly includes a catheter, including an inner member and a sheath, extending from a handle. The handle includes a housing, a braking assembly, a carriage and a carriage driver. The braking assembly comprises a braking element within the housing interior and a braking element rotator. The carriage comprises at least one carriage braking surface engaging the braking element. The carriage driver, such as a spring, biases the carriage towards the proximal end of the handle. The inner member has a proximal end secured to the housing. The sheath has a proximal end secured to the carriage. Rotating the braking element causes the carriage to move proximally as the carriage braking surface slides along the braking element. This causes the sheath to move proximally relative to the inner member.

36 Claims, 10 Drawing Sheets

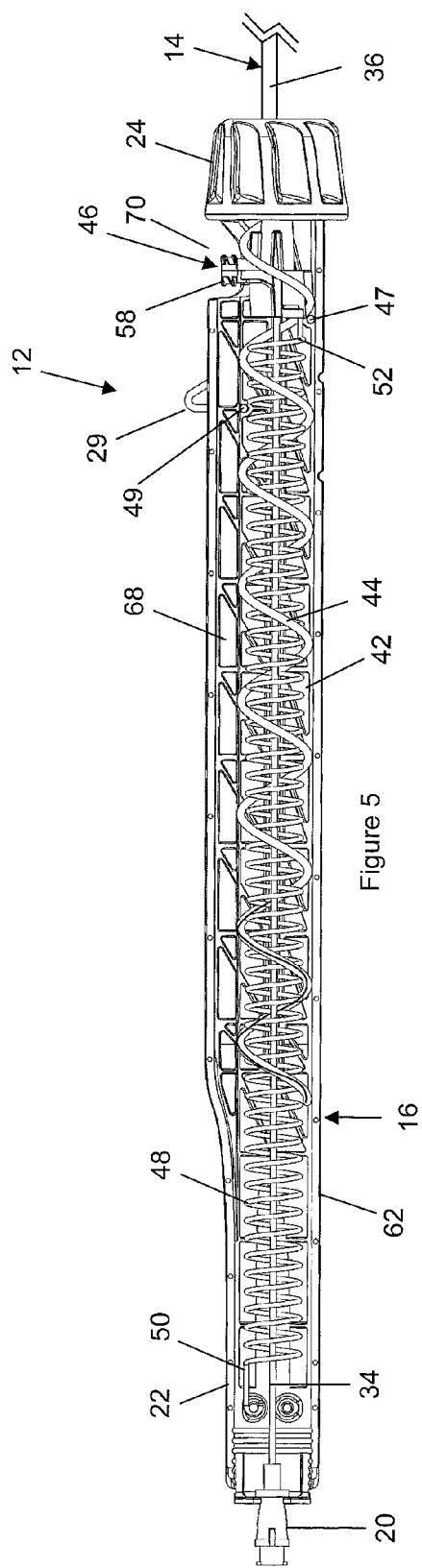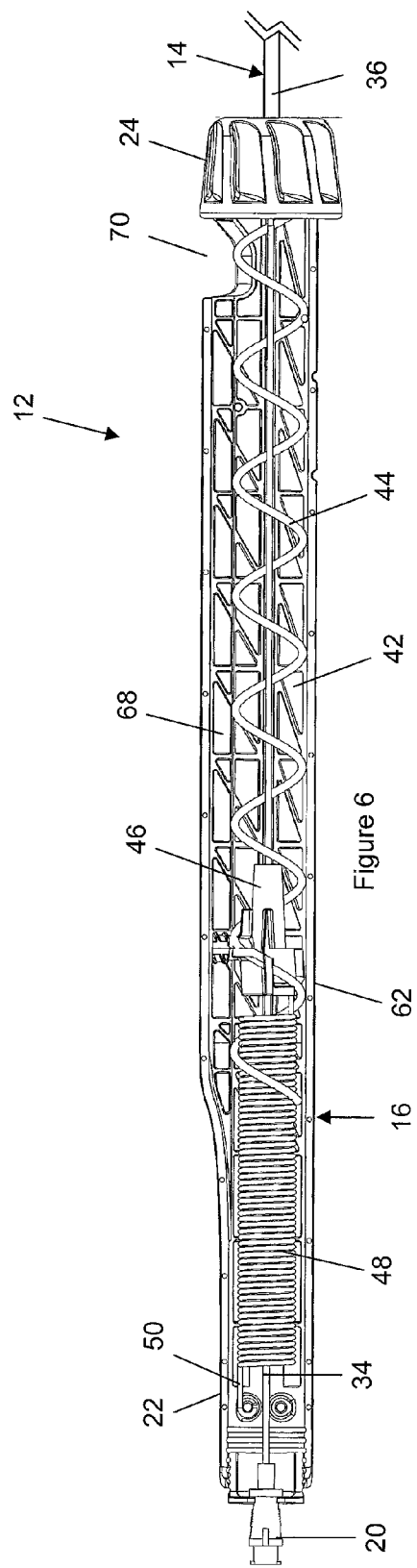

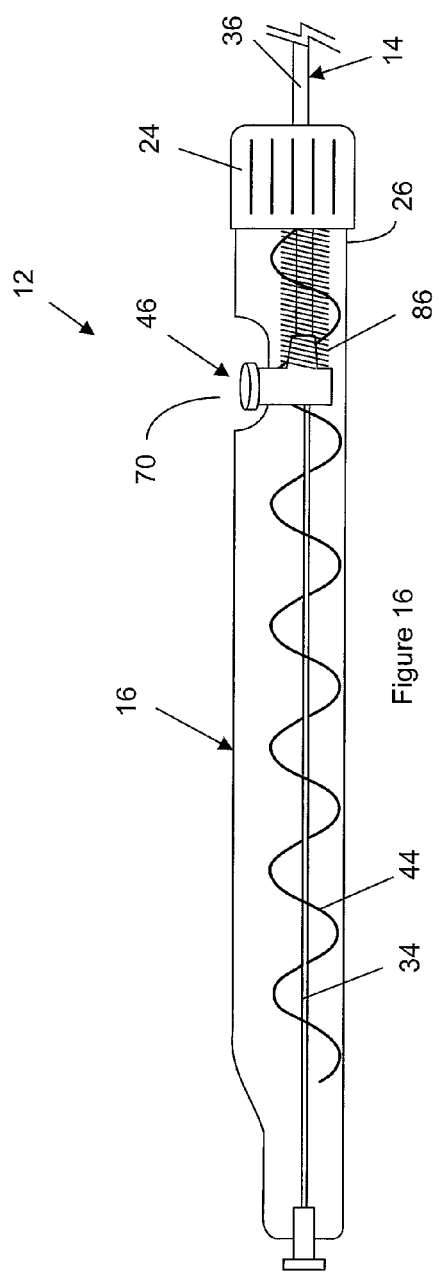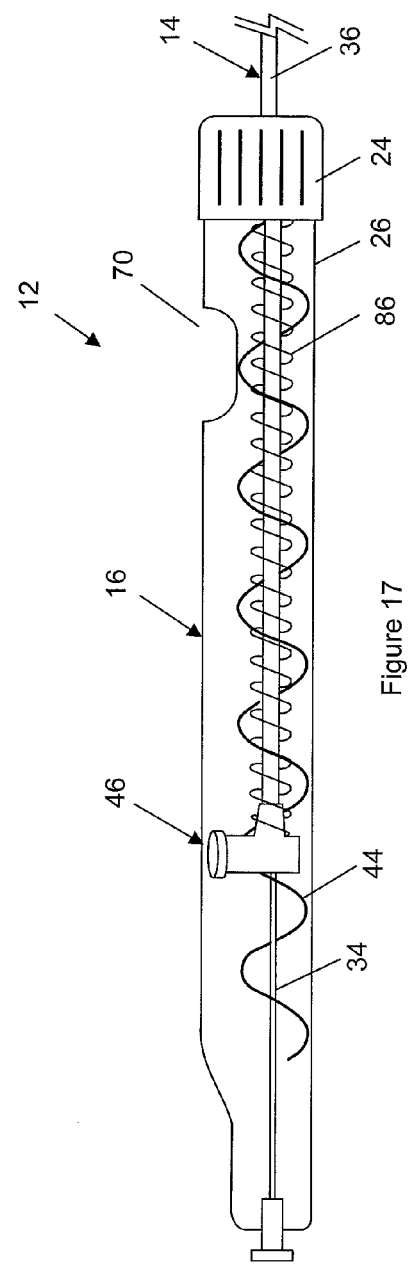

CATHETER ASSEMBLY WITH USER-ASSISTING HANDLE

BACKGROUND OF THE INVENTION

The present invention relates to a handle for implant deployment and to an associated deployment assembly. Delivery devices have long been used for a variety of medical procedures including maintaining passages, cavities or lumens in vessels, organs or ducts, occlusion of such vessels, delivering medical treatments, and other interventions. Today, there is a wide range of intravascular prostheses on the market for use in the treatment of aneurysms, stenosis, and other vascular disorders. Stents, stent grafts, and other vascular prostheses are well known for treating a myriad of diseases and illnesses in vasculature. For percutaneous interventions, many vascular prostheses are inserted into the body within a catheter and deployed at the desired treatment site. The present invention relates to a device for controlled deployment of a vascular prosthesis, such as a stent, stent-graft, filter or occlusion device, for treatment of vascular disorders.

Previously known vascular prostheses can be retained in a catheter delivery configuration using an outer sheath; the prosthesis then expands when the outer sheath is retracted or is subsequently expanded, for example, by a balloon. See, for example, US patent publication number US 2008/0021657 A1, assigned to the assignee of this application. Due to this configuration, several potentially undesirable effects are present during deployment of the prosthesis. Because the outer sheath may be restraining the prosthesis, the frictional force between the prosthesis and outer sheath must be overcome to deploy the stent. The frictional force may be prohibitive to easy sheath withdrawal, and the effort to deliver adequate force may shift the position of the prosthesis.

It is typically desirable that a vascular prosthesis have a high outward acting force to improve in vivo performance. However, this high outward acting force can result in a high frictional force during deployment, particularly at initiation of deployment. Overcoming a high deployment force can be undesirable from safety, ergonomic, and control perspectives, e.g. placement accuracy. A high deployment force requires the user to apply a high force to initiate and complete the deployment, likely with varying forces throughout the deployment. Additionally, prostheses are typically available in multiple configurations, e.g. length and diameter, causing variations in deployment forces required.

BRIEF SUMMARY OF THE INVENTION

This application is directed to systems in which vascular prostheses are retained in their contracted states or are otherwise protected through the use of an outer delivery sheath. Portions of the vascular prosthesis may be secured to an inner delivery catheter, an element to control the position of the prosthesis such as a pushing rod or a hollow tube allowing passage of a guidewire, as in US 2008/0221657 A1, or an inner delivery catheter may be unsecured and separate from the prosthesis.

Some deployment systems include handles which require handle manipulation with varying levels of force and often require the use of two hands. Some examples made according to the present invention provide handles which require a low and consistent force to result in a controlled deployment using one or two hands, independent of the implant configuration. This low and consistent force feature is an important advantage of such examples of the invention. To deploy the system, in some of the presented examples, the operator rotates a knob or similar feature to provide controlled retraction of an outer sheath used to restrain the implant. Rotating the knob controllably releases a driving force attached to the outer sheath.

An example of a catheter assembly includes a catheter and a handle. The catheter includes an inner member and a sheath housing the inner member and axially slidable over the inner member. The handle includes a housing, a braking element assembly, a carriage, and a carriage driver. The housing has a proximal end, a distal end, an inner surface, and a housing axis. The inner surface defines a housing interior. The braking element assembly includes an elongated braking element located within the housing interior and a braking element rotator operably coupled to the braking element for selective rotation of the braking element about the housing axis. The carriage is located within the housing interior and is movable along the housing axis. The carriage has at least one carriage braking surface engaging the braking element. The carriage driver biases the carriage towards the proximal end of the handle. The inner member has a proximal end secured to the housing. The sheath has a proximal end secured to the carriage. Operation of the braking element rotator causes the braking element to rotate in a first rotary direction allowing the carriage to move in a proximal direction, so that the sheath moves proximally relative to the inner member.

In some examples, the sheath is movable in a proximal direction relative to the inner member from a first position to a second position; in such examples, the catheter includes a distal end and a vascular prosthesis at the distal end, the vascular prosthesis being in contact with the inner member and being at least partially covered by the sheath when the sheath is in the first position, the vascular prosthesis being at least substantially uncovered by the sheath when the sheath is in the second position. In some examples, the braking element includes a helical element. When the braking element includes the helical element, in some examples, the helical element includes helical element portions with different pitches so that the amount of the axial movement of the carriage through the rotation of the helical element will depend on where the carriage is engaging the helical element. In some examples, the braking element defines an interrupted braking path; the interrupted path may include curved path sections joined by connecting sections.

In some examples, the braking element rotator includes a user-rotatable deployment knob rotatably mounted to the housing; the deployment knob and the housing may include anti-reverse elements to allow the deployment knob to rotate in one direction only. In some examples, the housing and the carriage define guide elements to aid limiting the movement of the carriage to movement along the housing axis. In some examples, the carriage driver includes a tension spring having a proximal end coupled to the proximal end of the housing and a distal end coupled to the carriage so that the tension spring exerts a tension force pulling the carriage in a proximal direction. In some examples, the carriage driver includes a compression spring captured between the carriage and the distal end of the housing so that the compression spring exerts a proximally directed force against the carriage.

Other features, aspects and advantages of the present invention can be seen on review of the figures, the detailed description, and the claims which follow.

BRIEF DESCRIPTION OF THE DRAWINGS

FIG. 5 is a cross-sectional view of the handle of FIG. 1 with one half of the housing removed to show internal components, the handle including a tension spring and shown in a pre-deployment state corresponding to the state of the vascular prosthesis of FIG. 2;

FIG. 6 shows the structure of FIG. 5 in a post-deployment state corresponding to the state of the vascular prosthesis of FIG. 4;

FIG. 16 is a simplified cross-sectional view illustrating a handle of a type comprising a compression spring in a pre-deployment state corresponding to the state of the vascular prosthesis of FIG. 2;

FIG. 17 shows the structure of FIG. 16 posted deployment state corresponding to the state of the vascular prosthesis of FIG. 4, the example of FIGS. 16 and 17 showing a single point of contact between helical element 44 and carriage 46 as opposed to the two points of contact shown in FIGS. 11 and 12;

DETAILED DESCRIPTION OF THE INVENTION

Figure 1:
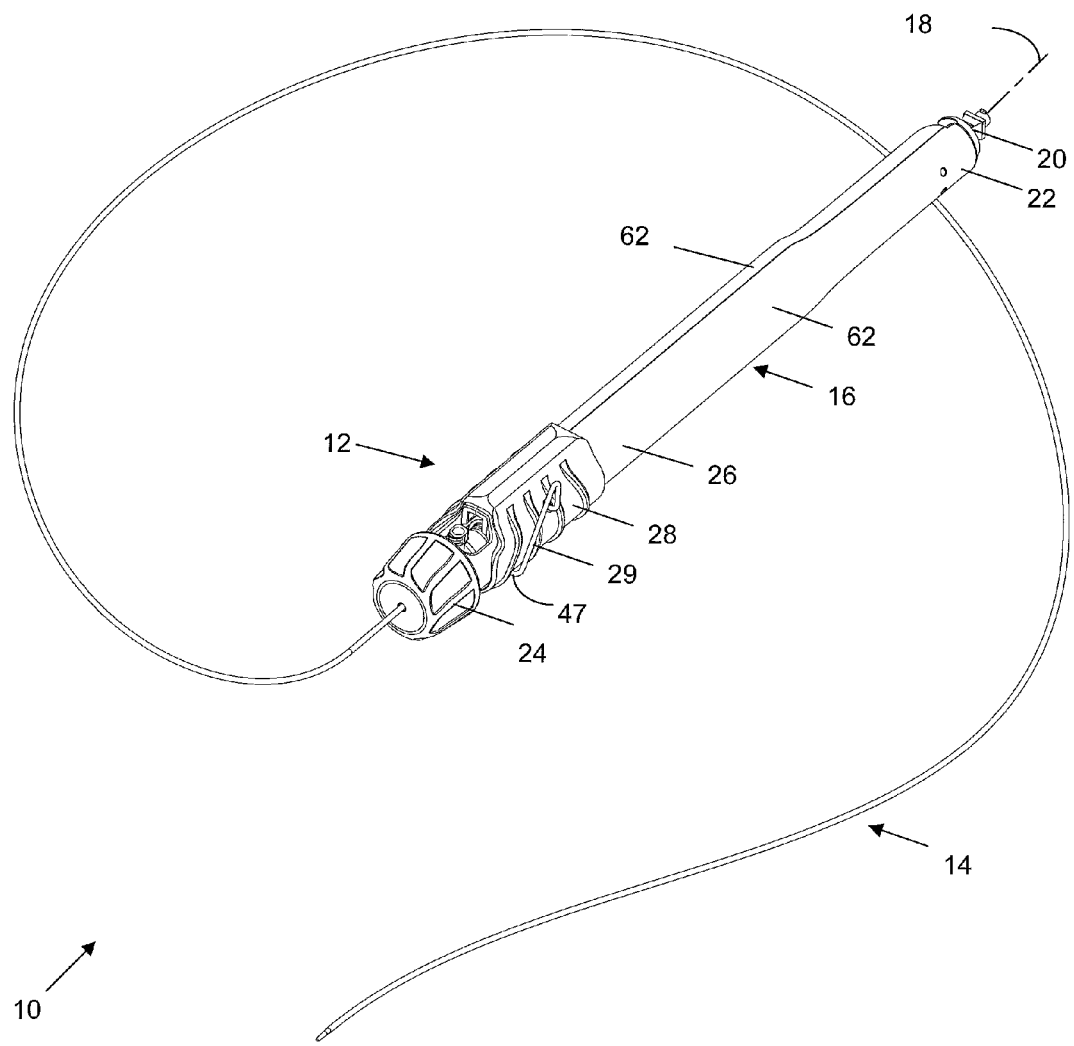
FIG. 1 illustrates one example of a catheter assembly made according to the invention, the catheter assembly including a handle and a catheter extending from the handle.

The following description will typically be with reference to specific structural embodiments and methods. It is to be understood that there is no intention to limit the invention to the specifically disclosed embodiments and methods but that the invention may be practiced using other features, elements, methods and embodiments. Preferred embodiments are described to illustrate the present invention, not to limit its scope, which is defined by the claims. Those of ordinary skill in the art will recognize a variety of equivalent variations on the description that follows. Like elements in various embodiments are commonly referred to with like reference numerals.

FIG. 1 illustrates one example of a catheter assembly 10 including a handle 12 and a catheter 14. Handle 12 includes a housing 16 defining a housing axis 18 with a flush port 20 at a proximal end 22. Handle 12 has a deployment knob 24 rotatably mounted to the distal end 26 of housing 16. Housing 16 also has a handle grip 28 at its distal end 26. A locking pin 29 is used to maintain the catheter assembly 10 in a pre-deployment state shown in FIG. 5.

Figure 2:
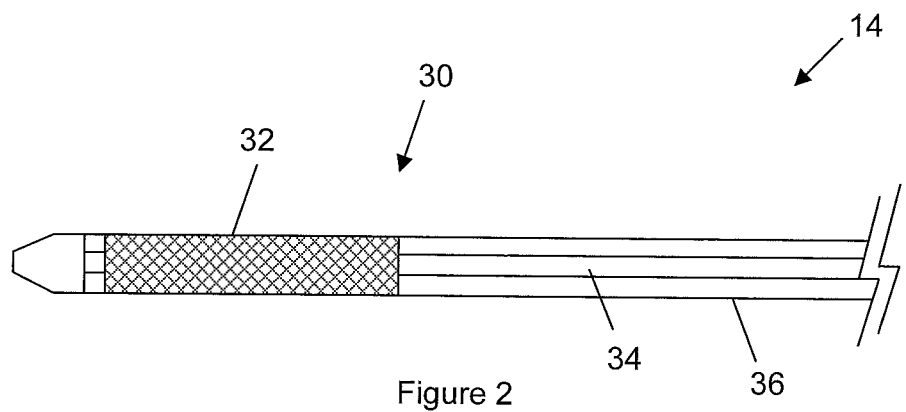
FIG. 2 is a simplified enlarged side view of the distal end of the catheter of FIG. 1 showing a vascular prosthesis in a radially contracted state mounted on the distal end of an inner member of the catheter with a sheath surrounding the vascular prosthesis.
Figure 3:
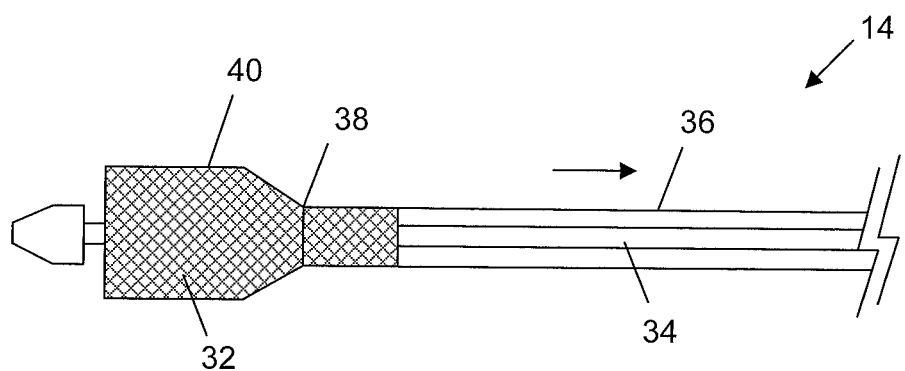
FIG. 3 shows the structure of FIG. 2 with the sheath pulled a short distance proximally thereby exposing a distal portion of the vascular prosthesis allowing the distal portion to assume a radially expanded state.
Figure 4:
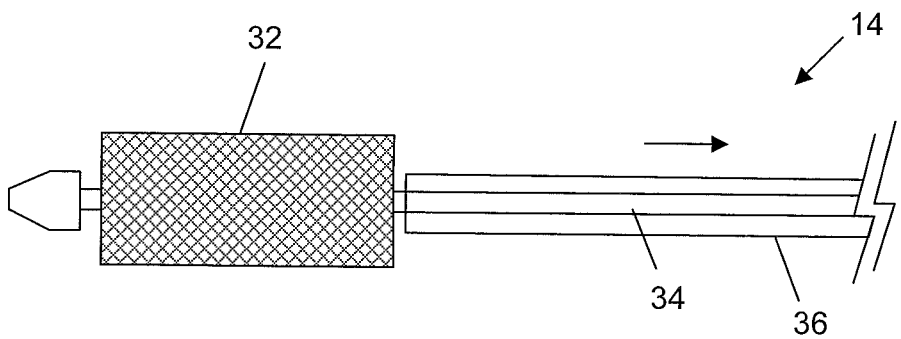
FIG. 4 shows the structure of FIG. 3 after the sheath has been pulled proximally an additional distance allowing the entire vascular prosthesis to assume a radially expanded state.

FIG. 2 is a simplified enlarged cross-sectional view of the distal end 30 of catheter 14. A vascular prosthesis 32, typically a self expanding stent, is shown in a radially contracted, pre-deployment state mounted on the distal end of an inner member 34 of catheter 14. Also illustrated is a sheath 36 surrounding the entire vascular prosthesis 32 to maintain the vascular prosthesis in the radially contracted, pre-deployment state. In FIG. 3 the structure of FIG. 2 is shown with sheath 36 pulled a short distance proximally with the distal end of the sheath shown at position 38. Doing so exposes a distal portion 40 of vascular prosthesis 32. This action may allows the distal portion to assume an expanded state, if self-expanding design. FIG. 4 shows vascular prosthesis 32 after sheath 36 has been pulled proximally an additional distance so that the entire vascular prosthesis 32 is exposed. The prosthesis may assume a radially expanded, post-deployment state.

FIG. 5 is a cross-sectional view of handle 12. Housing 16 of handle 12 has an interior 42 holding three main components: a helix assembly 43, also called a braking assembly 43, a carriage 46 and a tension spring 48. Helix assembly 43 includes a helical braking element 44, sometimes referred to as helix 44, secured to and rotatable by deployment knob 24. Therefore, deployment knob 24 acts as a helical element rotator. Instead of manually actuated deployment knob 24, the helical element rotator may comprise a motor drive coupled to helical element 44.

Figure 12:
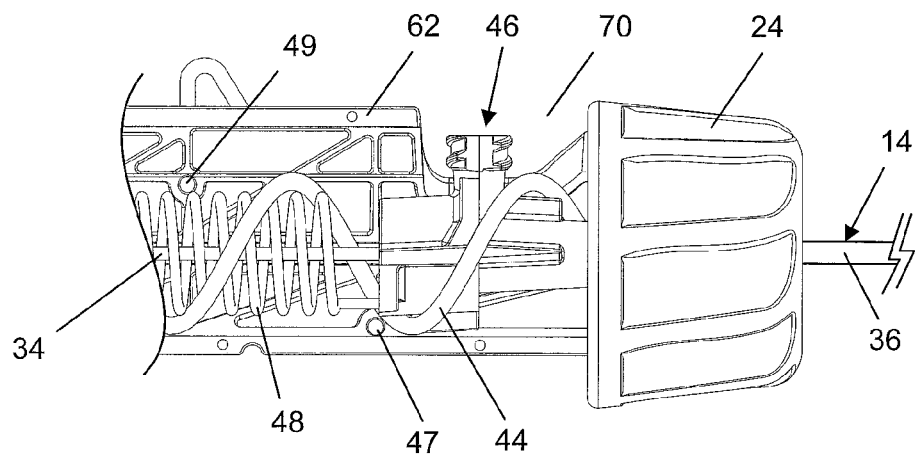

Helical element 44 is a helical wire having a circular cross-sectional shape. However, other cross-sectional shapes, such as rectangular, may also be used. While helical wires having round cross-sectional shapes may be easy to manufacture, a helical wire having, for example, a rectangular cross-sectional shape may be used based upon the desired frictional characteristics between braking element 44 and carriage 46 or improved strength with reduced handle size. Carriage 46 is movable through interior 42 along housing axis 18. Tension spring 48 is secured at its proximal end 50 to the proximal end 22 of housing 16 and at its distal end 52 to carriage 46. The structure of FIG. 5 is shown in its pre-deployment state corresponding to the pre-deployment state of vascular prosthesis 32 of FIG. 2. Tension spring 48 exerts a proximally directed force on carriage 46 thereby biasing the carriage in a proximal direction towards the post deployment state shown in FIG. 6, which corresponds to the post deployment state of vascular prosthesis 32 in FIG. 4. As described below, in this example, carriage 46 can move along housing axis 18 only when a user rotates deployment knob 24. Locking pin 29 is used to prevent inadvertent axial movement of carriage 46. Locking pin 29 has legs 47, 49, shown also in FIGS. 1 and 12, which pass through openings in housing 16. Leg 47 is positioned to maintain catheter assembly 10 in the pre-deployment state by preventing carriage 46 from moving proximally even if the user attempts to rotate deployment knob 24. Only after removal of locking pin 29 can a user freely rotate deployment knob 24. Locking pins or similar features may be used to directly block the motion of the carriage 46 or the rotation of the helix assembly 43. Alternatives to locking pins are considered and may include a sliding locking feature or a constraining clip.

Figure 7:
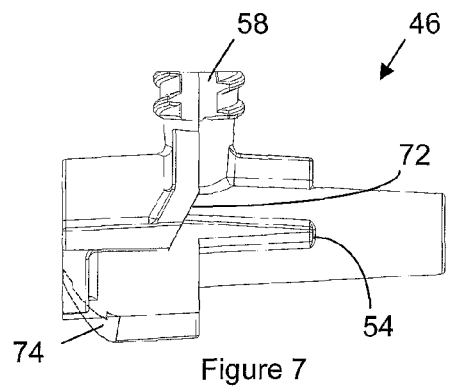
FIG. 7 is an enlarged side view of the carriage of FIG. 5 showing a first and second braking surfaces which engage the turns of the helical element.
Figure 8:
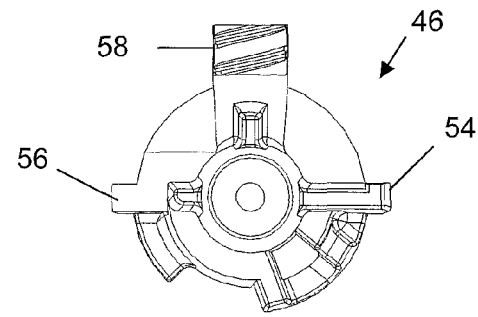
FIG. 8 is a proximally facing end view of the carriage of FIG. 7.
Figure 9:
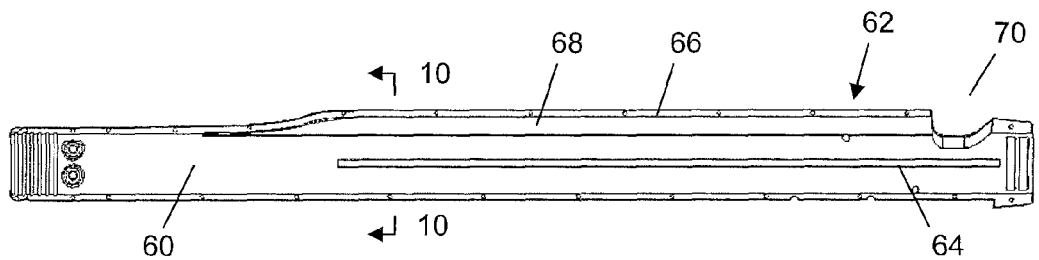
FIG. 9 is a side view of the inside surface of one half of the housing of the handle of FIGS. 1 and 2 showing the axially extending slot sized for receipt of radially extending fins of the carriage of FIGS. 7 and 8, and also showing an axially extending pathway sized for receipt of the flush port of the carriage of FIGS. 7 and 8.
Figure 10:
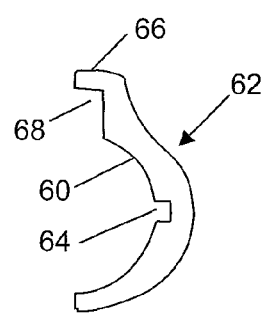
FIG. 10 is a cross-sectional view taken along line 10-10 of FIG. 9 showing the axially extending slot and the axially extending pathway.
Figure 11:
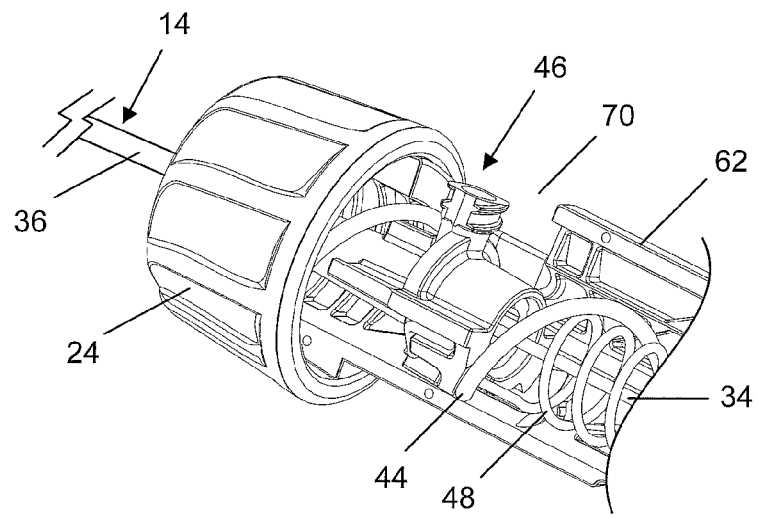
FIGS. 11 and 12 are enlarged isometric and side elevation views of the distal portion of the structure of FIG. 5.

FIGS. 7 and 8 are enlarged side and end views of carriage 46 showing laterally extending fins 54, 56 and an upwardly extending flush port 58. FIGS. 9 and 10 are side and cross-sectional views showing the inside surface 60 of one half 62 of housing 16, the opposite half being a substantial mirror image thereof. These views illustrate axially extending slot 64 sized for receipt of radially extending fins 54. The opposite half of housing 16 may have a similar slot configured for receipt of fin 56. The engagement of fins 54, 56 within slots 64 permits the axial movement of carriage 46 within the housing 16 but effectively prevents any other motion within the housing.

Sheath 36 is secured to and terminates at carriage 46 while inner member 34 passes through carriage 46 and terminates at flush port 20. Flush port 20 is secured to the housing 16. Carriage 46 is constructed so that flush port 58 is fluidly coupled to a region between inner member 34 and sheath 36. When in the pre-deployment state of FIG. 5, flush port 58 is aligned with a cutout 70 at the distal end 26 of housing 16. This provides user access to flush port 58 to permit the user to flush the region between inner member 34 and a sheath 36.

Housing halves 62 of housing 16 have axial extensions 66 which define an axially extending pathway 68 within the housing 16. Pathway 68 extends proximally from cutout 70 and having a length about equal or greater than the stent length to allow motion of carriage equal or greater than the stent length. Pathway 68 is sized to permit flush port 58 to move axially along pathway 68 as carriage 46 moves axially through housing 16. The configuration of pathway 68 also limits the rotation of carriage 46 around housing axis 18 once flush port 58 has moved from cutout 70 into pathway 68.

The interaction between carriage 46, handle housing 16 and helical element 44 will now be discussed primarily with reference to FIGS. 7, 8, 11 and 12. Tension spring 48 provides a force on carriage 46 tending to drive carriage 46 in a proximal direction, thus also pulling sheath 36 proximally relative to inner member 34. Such movement is what causes the exposure of vascular prosthesis 32 as shown in FIGS. 2-4. The free movement of carriage 46 is prevented by the engagement of helical element 44 with carriage braking surfaces 72, 74 on carriage 46; in addition, additional braking surfaces may be created, for example, between braking element 44 and housing 16, between deployment knob 24 and the housing, and between carriage 46 and the housing. Carriage braking surfaces 72, 74, in some examples, are generally spaced apart to help center carriage 46 within the housing 16. In this example, carriage braking surfaces 72, 74 are generally located on opposite sides of carriage 46. Rotation of deployment knob 24 causes helical element 44 to rotate about housing axis 18; this allows carriage 46 to move axially in a proximal direction thus moving sheath 36 proximally relative to inner member 34. The force on carriage 46, and thus on sheath 36, is typically due entirely to the tension force of spring 48 pulling on carriage 46; in some situations a part of the driving force on carriage 46 over a portion of its length of travel may be provided by the rotation of helical element 44. That is, through the use of spring 48, the user is not required to provide some or typically any of the force necessary to pull back sheath 36 over inner member 34. In a preferred configuration the tension spring 48 provides all the force necessary to do this while rotation of the deployment knob 24 overcomes other friction forces tending to hold helix assembly 43 in place.

The use of the helical element 44 provides control of the transmission force provided by the spring to move sheath 36 over inner member 34 upon rotation of deployment knob 24; it applies a braking force against the tendency of tension spring 48 to pull carriage 46, and thus sheath 36, proximally when deployment knob 24 is not being rotated by a user. The use of helical element 44 and deployment knob 24 helps dampen the difference in deployment force between units, which is felt by the physician or other user. The force required to rotate braking element assembly 43 is in a large part determined by the friction of braking assembly 43, including deployment knob 24 and braking element 44, against the housing 16 and the carriage 46.

Figure 13:
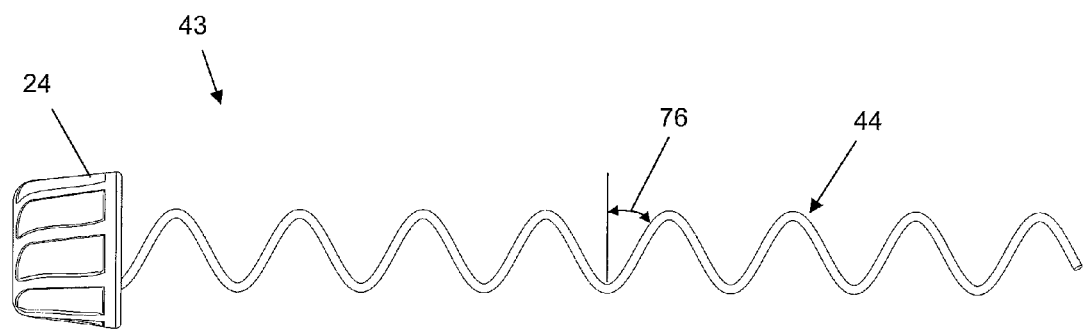
FIG. 13 is a side elevation view of the helix assembly of the handle of FIG. 5 showing the helical element having a constant pitch and a constant pitch angle.

In this example, the pitch angle 76 of helical element 44, see FIG. 13, is about 45°. The amount of force to be exerted by tension spring 48 on carriage 46 is preferably chosen to be at least about 10% higher than the amount of force required to move sheath 36 from the position of FIG. 2 to the position of FIG. 4 to reduce the possibility of inadequate force to drive the sheath retraction. The choices for the pitch angle 76 of helical element 44 and the force exertable by tension spring 48 provide a sound basis for designing catheter assembly 10 so that the amount of force required to rotate deployment knob 24 a reasonably small, comfortable level of force. In some examples, the configuration of braking surfaces 72, 74 may also be used in creating with an appropriate design. As mentioned above, other braking forces may be created by the friction of helical element 44 and deployment knob 24 rubbing against housing 16. The frictional force between deployment knob 24 and housing 16 may be adjusted by, for example, the use of higher friction or lower friction washers between deployment knob 24 and housing 16. The coefficient of friction between helical element 44 and carriage 46 or between helix assembly and housing 16 may, in some situations, also be chosen to achieve a desired level of force that must be exerted by the user when rotating deployment knob 24.

While the difference between the force exerted by spring 48 and the force needed to move the sheath 36 over inner member 34 can vary substantially between devices and clinical situations, the force to rotate the knob has less variability as a result of friction being to a large part unrelated to these forces. This results in a smooth and consistent deployment.

Figure 23:
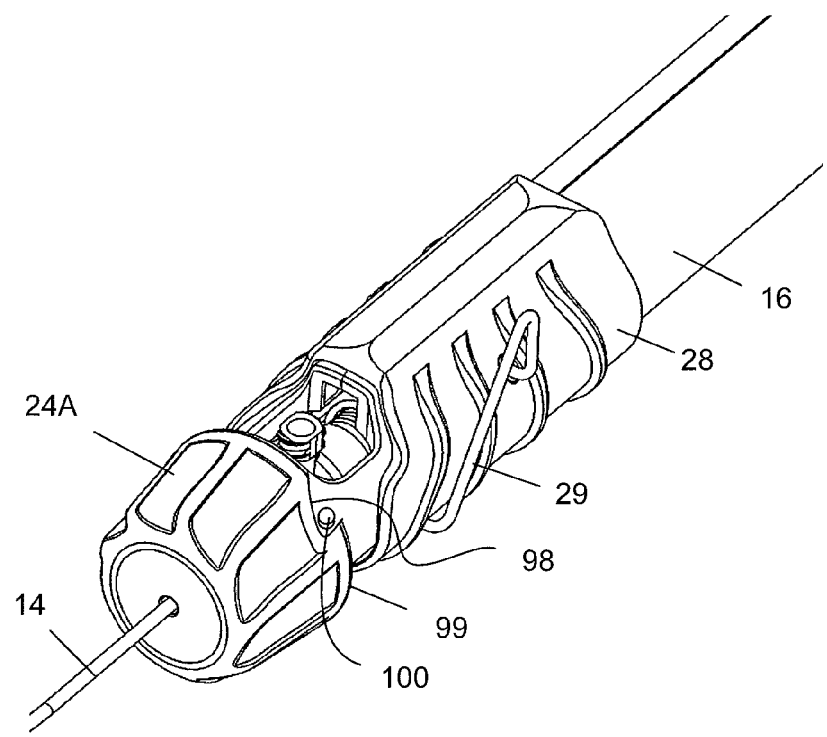
FIG. 23 illustrates an anti-reverse, ratcheting mechanism used to prevent rotating the deployment knob in a reverse direction, that is the direction that would cause the carriage to move distally.

Some examples may be designed to prevent the rotation of deployment knob 24 in the direction, termed the reverse direction, which would cause carriage 46 to move in a proximal direction. One way to do this is shown in FIG. 23. Deployment knob 24A has one or more anti-reverse cutouts 98 formed along its proximal edge 99 position to engage an outwardly extending peg 100 extending from housing 16. An example of FIG. 23, clockwise rotation of deployment knob 24A is permitted while counterclockwise rotation is prevented by the engagement of peg 100 within cutouts 98. Peg 100 may be sufficiently flexible so that it will bend in a proximal direction as deployment knob 24A is rotated in a clockwise direction. Alternatively, peg 100 may be spring mounted in a slot, not shown, formed in housing 16 permit the peg to be biased in a proximal direction to permit the clockwise rotation of deployment knob 24A. Other alternatives are also possible.

Figure 24:
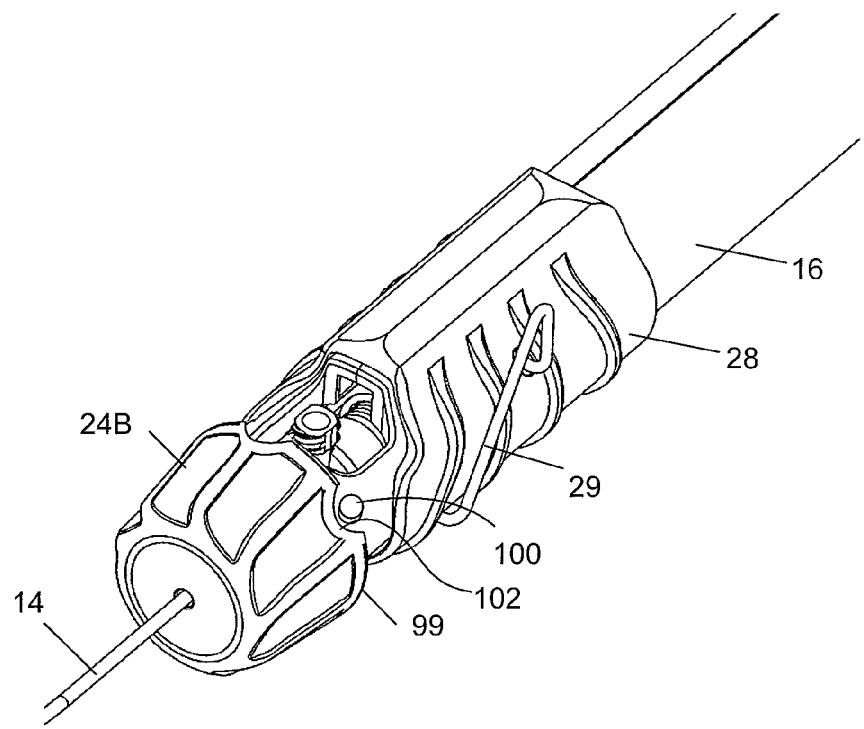
FIG. 24 is a view similar to that of FIG. 23 showing the use of a detent mechanism associated with the deployment knob to provide the user with visual, tactile and/or audible feedback relative to the rotation of the deployment knob.

Some examples may also be designed to provide tactical, auditory and visual feedback indicating the amount of rotation of deployment knob 24. FIG. 24 illustrates one example in which deployment knob 24B has a series of shallow cutouts 102 formed along its proximal edge 99 and within which a peg 100 is positioned when the two are aligned. The shallow, generally symmetrical shape of cutouts 102 permit the rotation of deployment knob 24B in either rotary direction while providing the desired tactile, auditory and/or visual feedback. Both the anti-reverse structure of FIG. 23 and the detent structure of FIG. 24 help to prevent inadvertent rotation of deployment knob 24. Peg 100 could be spring loaded in a slot formed in housing 16 to eliminate axial movement of deployment knob 24. Cutouts 98, 102 can also be created along an interior surface of deployment knob 24 so that neither the cutouts 98, 102 nor the peg 100 would be visible during use. Also, cutouts 98, 102 could be formed in housing 16 with a suitable cutouts-engaging member being carried by deployment knob 24.

Figure 14:
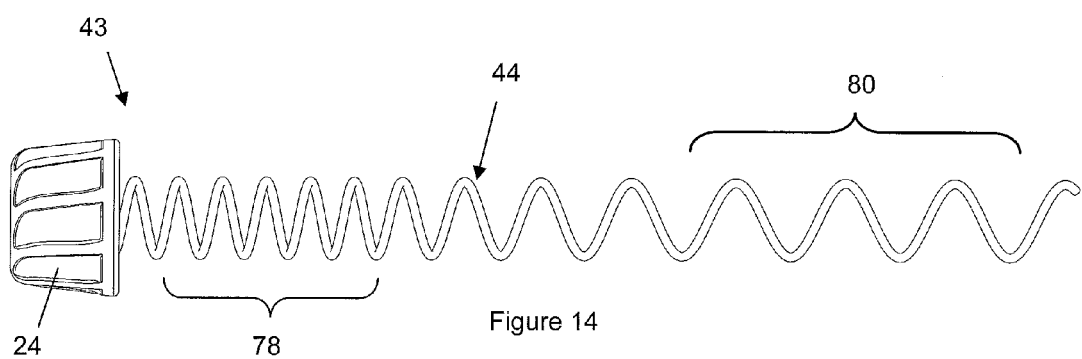
FIG. 14 is a side elevation view of a helix assembly with the helical element having a variable pitch with the distal turns having a shorter pitch than the proximal turns for enhanced control during the initial movement of the sheath from the pre-deployment state of FIG. 2.

In some examples, the pitch of the turns of the helical element may be varied over the length of the helical element. One example is shown in FIG. 14. In this example, helical element 44 has a variable pitch with the distal turns 78 having a shorter pitch, and thus a smaller pitch angle, than the proximal turns 80. This configuration provides for enhanced control during the initial movement of the sheath from the state of FIG. 2 because it takes more turns of deployment knob 24 to move carriage 46, and thus sheath 36, the same axial distance during the initial deployment when moving from the pre-deployment state of FIG. 2 towards the partially deployed state of FIG. 3 as it does during the final deployment when moving from a partially deployed state to the fully deployed state of FIG. 4.

Helical element 44 of FIGS. 13 and 14 each define an uninterrupted generally helical path. However, helical element 44 may also be made having an interrupted helical path. One way to create an interrupted helical path would be to have an abrupt transition between two helical sections so that there would be a discontinuity or corner, not a smooth transition, between the two helical sections. Another way to create an interrupted helical path is to join two helical sections by a connecting section, the connecting section comprising, for example, one or more of the axially straight segments and a segment having a generally constant axial position and a changing rotary position. Each helical section may be a partial or a complete rotation about the axis. The length of the helical section determines the degree of rotation of the knob required.

Figure 18:
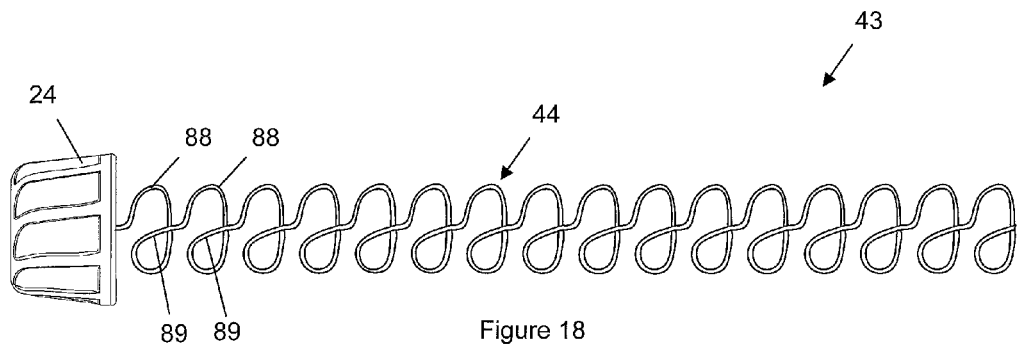
FIGS. 18-21 illustrate three different braking element assemblies including interrupted braking paths.
Figure 19:
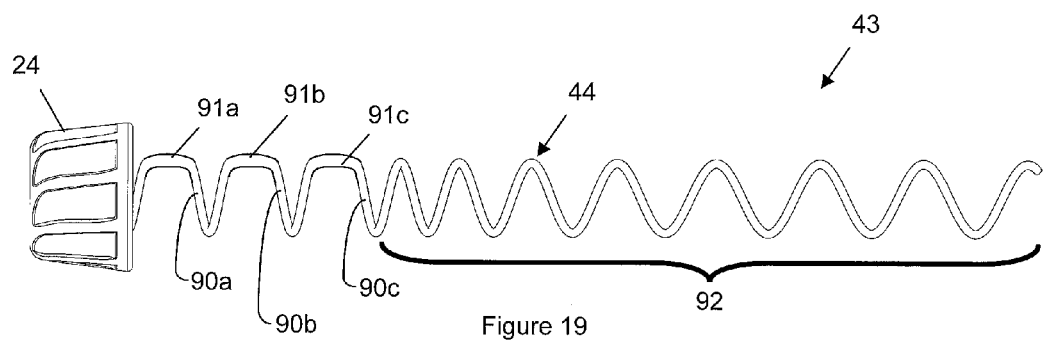
Figure 20:
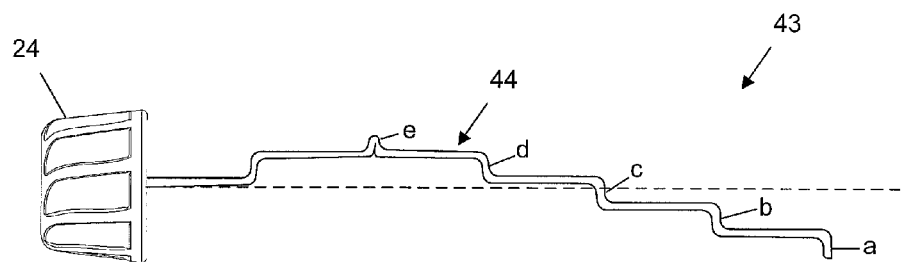
Figure 21:
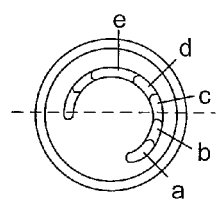

FIGS. 18-21 illustrate three different braking element assemblies 43 including interrupted braking paths. In the example of FIG. 18, braking element 44 includes a series of full, generally helical turns 88 coupled by generally straight, generally axially-extending connecting sections 89 so that movement of carriage 46 along connecting sections 89 is more rapid than along generally helical turns 88. In FIG. 19 braking element assembly 43 includes a braking element 44 comprising a short series of generally 180° helical turns 90 connected by axially extending sections 91 so that the movement of carriage 46 along section 91 is quite rapid compared to movement along turns 90. Turns 90 and sections 91 are followed by a continuous helical section 92 having a variable pitch. FIGS. 20 and 21 illustrate another design of braking element assembly 43; braking element 44 extends along a helical path of less than one complete turn over its entire length as shown in FIG. 21. This is a somewhat extreme example of a situation in which carriage 46 will not move, or will only move small distances, when carriage is engaging the circumferentially extending segments, such as segments a-e in the figures, but will move quite rapidly while engaging the axially extending segments between the circumferentially extending segments.

Figure 15:
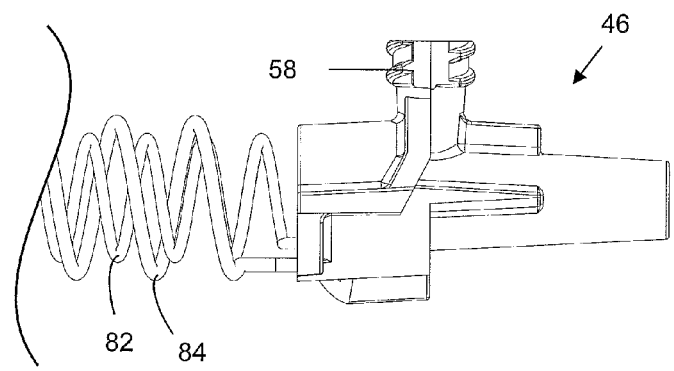
FIG. 15 shows the carriage of FIG. 11 with the distal ends of two nested tension Springs secured to the carriage.

Tension spring 48 lies generally concentrically within helical element 44 to save space within housing 16. The use of the tension spring 48 provides flexibility with force profile and a linear, non-buckling deployment. In some examples, nested springs may be used instead of the single tension spring 48. FIG. 15 illustrates an example showing nested tension springs 82, 84 having their distal ends secured to carriage 46. Nested tension springs 82, 84 are pitched opposite one another and have different pitches. That is, they are wound in opposite directions so as to prevent entanglement between the two springs. Having different pitches also helps to prevent entanglement.

The spring may be, for example, a metal spring, a non-metallic elastomeric spring, a tension spring, a compression spring, a constant force spring, a constant torque spring, or a combination thereof. One example of a compression spring is shown in FIGS. 16 and 17. FIG. 16 illustrates a handle of a type comprising a compression spring 86 in a pre-deployment state corresponding to the state of the vascular prosthesis of FIG. 2. Compression spring 86 is captured between carriage 46 and the distal end 26 of housing 16. FIG. 17 shows the structure of FIG. 16 and a post-deployment state corresponding to the state of the vascular prosthesis of FIG. 4. Springs 48, 82, 84 and 86 are examples of carriage drivers which bias carriage 46 towards the proximal end 22 of housing 16. Other types of carriage drivers, including one or more of a motor drive, an air cylinder drive, and a linear driver may also be used instead of or in addition to springs.

Figure 22:
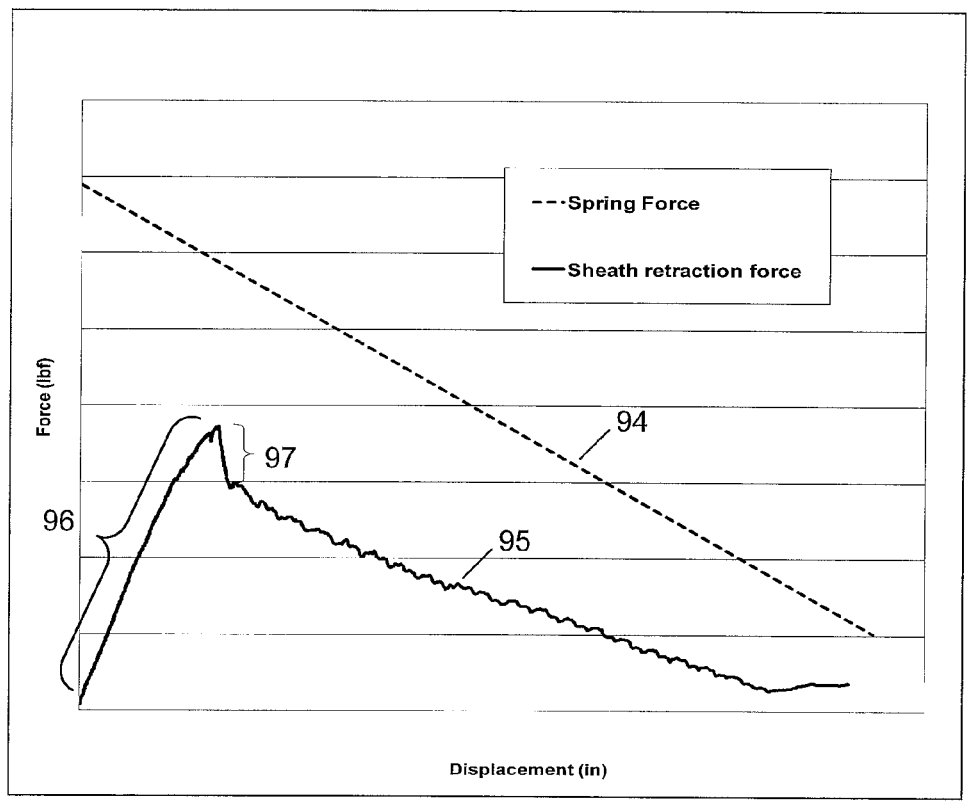
FIG. 22 is a graph illustrating force versus displacement for the spring and force versus displacement for the sheath.

FIG. 22 is a graph illustrating a force versus displacement plot 94 for spring 48 and a force versus displacement plot 95 for sheath 36. The initial portion 96 of plot 95 reflects the initial stretching of components of a catheter assembly 10, primarily sheath 36, before sheath 36 begins to move. A second portion 97 of plot 95 demonstrates a short, quick movement of sheath 36 following initial portion 96. The remainder of plot 95 illustrates the force versus displacement plot for sheath 36 as it is pulled by carriage 46. It is seen that the force exerted by spring 48 is always greater than the sheath retraction force.

An example of a method for making handle 12, for use with catheter 14, proceeds as follows. Carriage 46 is mounted within the interior 42 of housing 16 for movement along the housing axis 18, the carriage comprising carriage braking surfaces 72, 74 engaging helical element 44. The distal end of spring 48 is secured to carriage 46 while the proximal end of the spring is secured to proximal end 22 of housing 16. Deployment knob 24 of helix assembly 43 is positioned at the distal end of housing 16 in a manner to allow deployment knob 24 to rotate about housing axis 18. In one example, the deployment knob 24 is held against the distal end of housing 16 through the spring force of exerted on the carriage and resulting force on the helical element 44. In other examples, deployment knob 24 may be rotatably mounted to housing 16. Helical element 44 of helix assembly 43 extends into the interior 42 and engages braking surfaces 72, 74 of carriage 46. The proximal end of the inner member 34 of catheter 14 is secured to the proximal end 22 of the housing. The proximal end of sheath 36 is secured to carriage 46. The force required to move sheath 36 a distance in a proximal direction relative to inner member 34, referred to as the first force, is determined. The force to be exerted by spring 48 on carriage 46 to bias the carriage towards the proximal end of handle 12 is selected. The spring force is typically chosen to be greater than the first force. The pitch angle 76 for helical element 44 is selected. Carriage braking surfaces 72, 74 are configured for appropriate sliding frictional engagement with helical element 44. The spring force is selected and the pitch angle is selected so that deployment knob 24 must be rotated by the user to cause helical element 44 to rotate in a first rotary direction to cause carriage 46 to move in a proximal direction as helical element 44 slides along carriage braking surfaces 72, 74. Doing so causes sheath 36 to move proximally relative to inner member 34 thus exposing vascular prosthesis 32. In some examples, the spring force is at least 10% greater than the first force. In some examples, the spring force is chosen to be less than the strength of sheath 36 in tension. Note that if the spring force is chosen to be greater than the first force, making the pitch angle 76 excessively large may permit spring 48 to pull carriage 46 proximally without the need for the user rotating deployment knob 24. That is, the spring force exerted by spring 48 would be sufficient to cause helix assembly 43 to rotate by itself as sheath 36 is pulled proximally. In some cases this situation may be acceptable or desirable.

An example of a method for the operation of handle 12 can be carried out as follows. The user grasps handle 12 and removes locking pin 29. Deployment knob 24 is rotated by the user causing helical element 44 to rotate in a first rotary direction about the housing axis. Doing so causes carriage 46, and sheath 36 secured thereto, to move in a proximal direction. This movement is in response to both the rotation of the deployment knob 24 and the biasing of carriage 46 towards the proximal end of the handle by spring 48. In some examples, helical element 44 is a variable pitch helical element comprising a first, shorter pitch helical element portion 78 engageable with carriage 46 during an initial movement of the carriage and a second, longer pitch helical element portion 80 engageable with the carriage during subsequent movement of the carriage. In this way a single rotation of helical element 44 during the initial movement of the carriage 46 pulls sheath 36 a shorter distance than a single rotation of the helical element during the subsequent movement of the carriage to provide enhanced user control during the typically critical initial movement of the sheath.

An example of a method useful for when interrupted braking paths are used, such as would occur with the examples of FIGS. 18-21, can be carried out as follows. Assume braking element assembly 43 of FIG. 19 is used, and assume that helical turn 90a initially engages carriage braking surfaces 74, 76. Deployment knob 24 is rotated until carriage braking surfaces 74, 76 engage axially extending section 91b. During the engagement along helical turn 90a, rotating deployment knob 24 a first angular distance from a first angular orientation to a second angular orientation permits the carriage 46, and thus sheath 36, to move a first linear distance under the influence of spring 48.

During the engagement along axially extending section 91b, rotating deployment knob 24 a second angular distance from the second angular orientation to a third angular orientation permits carriage 46, and thus sheath 36, to move a second linear distance. In the example of FIG. 19, the second angular distance moved by deployment knob 24 is either a negligible amount or zero depending on the orientation and configuration of carriage braking surfaces 72, 74 and the shape and orientation of axially extending section 91b. When interrupted braking paths are used, the axial distance moved by carriage 46, and thus sheath 36 for the same rotation of deployment knob 24 is different for adjacent sections of braking element 44. Therefore, the ratio of the first angular distance to the first linear distance is different from the ratio of the second angular distance to the second linear distance. In some examples in which interrupted braking paths are used, the first and second angular distances are the same angular distances while the corresponding first and second linear distances are different. This could be achieved, for example, by having alternating helical sections have different pitches. In some examples, tactile feedback can be provided to the user during the rotation of deployment knob 24 to, for example, indicate when a transition is to be made between different sections.

The above descriptions may have used terms such as above, below, top, bottom, over, under, et cetera. These terms may be used in the description and claims to aid understanding of the invention and not used in a limiting sense.

While the present invention is disclosed by reference to the preferred embodiments and examples detailed above, it is to be understood that these examples are intended in an illustrative rather than in a limiting sense. It is contemplated that modifications and combinations will occur to those skilled in the art, which modifications and combinations will be within the spirit of the invention and the scope of the following claims. For example, rotation of the braking element 44 can be achieved using multiple methods, such as a triggering mechanism, gearing mechanism, a variable speed motor or belt drive mechanism. Deployment knob 24 can be attached to handle 12 at various positions including attachment to proximal end 22 of the handle. Springs can be parallel to but not concentric with carriage 46 and inner shaft member 34, perhaps through use of a drive plate to link them. Flush port 56 can remain exposed along its entire length of movement along the handle 12, such as by sliding within a slot formed along the handle housing 16.

The following clauses describe aspects of various examples of methods relating to catheter assembly handles.

1. A method for making a handle of a catheter assembly, the catheter assembly of a type comprising a catheter including an inner member and a sheath surrounding the inner member and axially slidable over the inner member, the sheath being movable in a proximal direction relative to the inner member from a first position to a second position, the method comprising:

mounting a braking element assembly to a housing of a handle, the housing defining a housing axis, the braking element assembly comprising a braking element mounted within the housing interior and a braking element rotator operably coupled to the braking element for selective rotation of the braking element about the housing axis;

mounting a carriage within the housing interior for movement along the housing axis, the carriage comprising a carriage braking surface engaging the braking element;

connecting a proximal end of the inner member to the housing;

connecting a proximal end of the sheath to the carriage;

determining an axially directed first force required to move the sheath in a proximal direction relative to the inner member from the first position to the second position;

selecting an axially directed second force to be exerted by the carriage driver on the carriage thereby biasing the carriage the towards the proximal end of the handle, selecting the second force to be greater than the first force;

biasing the carriage towards the proximal end of the handle using the second force; and carrying out the second force selecting step so that the second force is greater than the first force, the second force being insufficient to cause the carriage to move in a proximal direction without actuation of the braking element rotator, the first and second forces being variable forces according to the position of the sheath relative to the inner member between the first and second positions.

2. The method according to clause 1 further comprising:
determining the strength of the sheath in tension; and
the second force selecting step comprising limiting the selection of the second force to be less than the strength of the sheath in tension.

3. The method according to clause 1, wherein the second force selecting step is carried out so that the second force is at least 10% greater than the first force.

4. The method according to clause 1 further comprising carrying out the braking element mounting step, the carriage mounting step and the second force selecting step so that the second force is insufficient to cause the carriage to move in a proximal direction without actuation of the braking element rotator.

5. The method according to clause 1 wherein:
the braking element comprises a helical braking element portion having a pitch angle; and further comprising:
selecting the pitch angle for the helical braking element portion.

6. The method according to clause 5 wherein the second carrying out step comprises carrying out the pitch angle selecting step, the braking element mounting step, the carriage mounting step and the second force selecting step so that the second force is insufficient to cause the carriage to move in a proximal direction without actuation of the braking element rotator.

7. The method according to clause 5, wherein the pitch angle selecting step is carried out by selecting a variable pitch angle so that the amount of the axial movement of the carriage through the rotation of the helical element will depend on the where the carriage is engaging the helical braking element portion.

8. The method according to clause 7 wherein the variable pitch angle selecting step comprises selecting first and second pitches for first and second helical braking element portions with the first pitch being shorter than the second pitch, the first helical braking element portion engageable with the carriage during an initial movement of the carriage and the second helical braking element portion engageable with the carriage during subsequent movement of the carriage, whereby user control can be enhanced during initial movement of the helical braking element portion.

9. The method according to clause 1 further comprising limiting movement of the carriage to movement along the housing axis.

10. The method according to clause 1, wherein the braking element rotator comprises a user-rotatable deployment knob rotatably mounted to the housing.

11. The method according to clause 1, wherein the carriage mounting step is carried out using a carriage having a plurality of carriage braking surfaces.

12. The method according to clause 11, wherein the carriage mounting step further comprises orienting the carriage braking surfaces in directions to help maintain the carriage at a chosen position within the housing.

13. The method according to clause 1, further comprising:
selecting a carriage driver comprising a spring for use in the carriage biasing step; and
coupling the spring to the housing and to the carriage.

14. The method according to clause 13, wherein:
the braking element comprises a helical braking element, and further comprising: positioning the spring at least partly within the helical braking element.

15. The method according to clause 13, further comprising:
selecting a tension spring as the spring for use in the carriage biasing step, the tension spring having a proximal end and a distal end;
connecting the proximal end of the tension spring to the proximal end of the housing and the distal end of the spring to the carriage; and
exerting a force on the carriage by the tension spring thereby biasing the carriage in a proximal direction.

16. The method according to clause 13, further comprising:
selecting a compression spring as the spring for use in the carriage biasing step;
capturing the compression spring between the distal end of the housing and the carriage; and
exerting a force on the carriage by the compression spring thereby biasing the carriage in a proximal direction.

17. A method for the operation of a handle of a catheter assembly of a type comprising a catheter including an inner member and a sheath surrounding the inner member and axially slidable over the inner member, the sheath being movable in a proximal direction relative to the inner member, the method comprising:
grasping, by a user, the handle of the catheter assembly, the handle comprising:
a housing having proximal and distal ends, the housing defining a housing interior and having a housing axis;
a braking element assembly comprising a braking element located within the housing interior and a braking element rotator operably coupled to the braking element for selective rotation of the braking element about the housing axis;
a carriage located within the housing interior and movable along the housing axis, the carriage comprising at least one carriage braking surface engaging the braking element; and
the carriage being biased towards the proximal end of the handle by a carriage driver;
operating, by the user, the braking element rotator causing the braking element to rotate in a first rotary direction about the housing axis;
moving, in response to the operating step and the carriage being biased toward the proximal end of the handle:
the carriage in a proximal direction as the braking element moves along the carriage braking surface; and
the sheath proximally relative to the inner member.

18. The method according to clause 17 wherein the braking element rotator operating step is carried out by the user rotating a user-rotatable deployment knob rotatably mounted to the housing.

19. The method according to clause 17 wherein the grasping step is carried out with the braking element comprising a variable pitch helical braking element, and the moving step comprises moving the carriage variable axial distances according to where the carriage is engaging the helical braking element.

20. The method according to clause 19, wherein the variable pitch helical braking element comprises a first helical braking element portion engageable with the carriage during an initial movement of the carriage and a second helical braking element portion engageable with the carriage during subsequent movement of the carriage, the first and second helical braking element portions having first and second pitches, respectively, the first pitch being shorter than the second pitch, whereby the moving step comprises:

moving the carriage a first distance for a single rotation of the helical braking element during the initial movement of the carriage and a second distance for a single rotation of the helical braking element during the subsequent movement of the carriage, the first distance being shorter than the second distance, whereby user control can be enhanced during the initial movement of the helical braking element.

21. The method according to clause 17, further comprising providing feedback to the user during the braking element rotator operating step.

22. A method for use with a catheter assembly of a type comprising a handle and a catheter extending from the handle, the catheter including an inner member and a sheath surrounding the inner member and axially slidable over the inner member, the catheter assembly further comprising a vascular prosthesis adjacent to the inner member, the vascular prosthesis at least partially covered by the sheath when the sheath is at a distal sheath position, the method comprising:

rotating a rotator, carried by the handle, a first angular distance from a first angular orientation to a second angular orientation so that the sheath moves a first linear distance;

rotating the rotator a second angular distance from the second angular orientation to a third angular orientation so that the sheath moves in a second linear distance; and the ratio of the first angular distance to the first linear distance being different from the ratio of the second angular distance to the second linear distance.

23. The method according to clause 22 wherein the first and second angular distances are the same angular distances.

24. The method according to clause 22 wherein the first rotating step causes effectively no linear movement of the sheath so that the first linear distance is effectively zero, and the second rotating step causes the sheath to move a measurable linear distance.

25. The method according to clause 22 wherein the first rotating step causes a first linear movement of the sheath and the second rotating step causes a second linear movement of the sheath, the first and second linear movements causing the sheath to move first and second measurable linear distances.

26. The method according to clause 25 wherein the first and second measurable linear distances are different measurable linear distances.

27. The method according to clause 22 wherein the first and second rotating steps each comprise providing a tactile feedback to the user during the rotating steps.

28. The method according to clause 22 wherein at least one of the first and second rotating steps comprises providing feedback during said at least one of the rotating steps.

29. The method according to clause 22 wherein at least one of the first and second rotating step comprises providing visual, tactile and auditory feedback during said at least one of the rotating steps.

Any and all patents, patent applications and printed publications referred to above are incorporated by reference.

What is claimed is:

1. A catheter assembly comprising:
a catheter comprising an inner member and a sheath housing the inner member and axially slidable over the inner member;
a handle comprising:
a housing having a proximal end, a distal end and an inner surface, the inner surface defining a housing interior, the housing having a housing axis;
a braking element assembly comprising an elongate braking element located within the housing interior and a braking element rotator operably coupled to the braking element for selective rotation of the braking element about the housing axis;
a carriage located within the housing interior and movable along the housing axis, the carriage comprising at least one carriage braking surface engaging the braking element; and
a carriage driver biasing the carriage towards the proximal end of the handle;
the inner member having a proximal end secured to the housing;
the sheath having a proximal end secured to the carriage; and
whereby operation of the braking element rotator to cause the braking element to rotate in a first rotary direction allowing the carriage to move in a proximal direction, so that the sheath moves proximally relative to the inner member.

2. The catheter assembly according to claim 1, wherein the carriage driver comprises at least one of a spring, a motor drive, an air cylinder drive, and a linear driver.

3. The catheter assembly according to claim 1, wherein the carriage driver comprises a spring, the spring comprising a metal spring, elastomeric spring, a tension spring, a compression spring, a constant force spring, a constant torque spring, or a combination thereof.

4. The catheter assembly according to claim 1, wherein the carriage driver comprises a plurality of concentric springs.

5. The catheter assembly according to claim 1, wherein the carriage driver exerts a force on the carriage generally parallel to the axis.

6. The catheter assembly according to claim 1, wherein the sheath is movable in a proximal direction relative to the inner member from a first position to a second position.

7. The catheter assembly according to claim 6, wherein the catheter comprises a distal end and a prosthesis at the distal end, the prosthesis in contact with the inner member and being at least partially covered by the sheath when the sheath is in the first position, the prosthesis being at least substantially uncovered by the sheath when the sheath is in the second position.

8. The catheter assembly according to claim 7, wherein the prosthesis is a self-expanding stent.

9. The catheter assembly according to claim 6, wherein:
an axially directed first force is required to move the sheath from the first position to the second position;
the carriage driver exerts an axially directed second force on the carriage biasing the carriage proximally; and
the first and second forces are variable forces according to the position of the sheath relative to the inner member; and
the second force is greater than the first force at each position of the sheath relative to the inner member between the first and second positions.

10. The catheter assembly according to claim 9, wherein the second force is at least 10% greater than the first force.

11. The catheter assembly according to claim 1, wherein the braking element comprises a helical element.

12. The catheter assembly according to claim 11, wherein the helical element comprises a helical wire having a generally rectangular cross-sectional shape.

13. The catheter assembly according to claim 11, wherein the helical element comprises helical element portions with different pitches so that the amount of the axial movement of the carriage through the rotation of the helical element will depend on the where the carriage is engaging the helical element.

14. The catheter assembly according to claim 11, wherein the helical element comprises a first helical element portion engageable with the carriage during an initial movement of the carriage and a second helical element portion engageable with the carriage during subsequent movement of the carriage, the first and second helical element portions having first and second pitches, respectively, the first pitch being shorter than the second pitch, whereby axial movement of the carriage along the first helical element portion is slower than along the second helical element portion for the same rate of rotation of the helical element, whereby user control can be enhanced during initial movement of the helical element.

15. The catheter assembly according to claim 1, wherein the braking element defines an interrupted braking path.

16. The catheter assembly according to claim 15, wherein the interrupted path comprises curved path sections joined by connecting sections.

17. The catheter assembly according to claim 16, wherein:
at least one of the curved path sections define a curved path having a generally constant axial position and a changing rotary position; and
at least one of the connecting sections defines a path having a changing axial position.

18. The catheter assembly according to claim 16, wherein:
the curved path sections each define a curved path having a changing axial position and a changing rotary position; and
a plurality of the connecting sections define generally straight paths having changing axial positions.

19. The catheter assembly according to claim 15, wherein the braking path comprises a plurality of curved, generally helical sections joined by at least one connecting section.

20. The catheter assembly according to claim 19, wherein said at least one connecting section comprises a generally straight section extending generally parallel to the axis.

21. The catheter assembly according to claim 1, wherein the braking element rotator comprises a user-rotatable deployment knob rotatably mounted to the housing.

22. The catheter assembly according to claim 21, wherein the deployment knob is affixed to the braking element.

23. The catheter assembly according to claim 21, wherein the deployment knob is rotatably mounted to the distal end of the housing in a fixed axial position relative to the housing axis.

24. The catheter assembly according to claim 21, wherein the deployment knob and the housing comprises anti-reverse elements to allow the deployment knob to rotate in one direction only.

25. The catheter assembly according to claim 1, wherein the carriage has a plurality of spaced apart carriage braking surfaces contacting the braking element.

26. The catheter assembly according to claim 1, wherein:
the sheath and inner member define a first region therebetween;
the carriage comprises a flush port fluidly coupled to said first region;
the housing comprises a flush port access opening; and
the flush port being aligned with the flush port access region when the carriage is at a first position;
whereby the first region between the sheath and inner member may be flushed through the flush port.

27. The catheter assembly according to claim 26, wherein:
the flush port is a generally radially extending member; and
the housing has an axially extending extension defining an axially extending pathway along which the flush port can move as the carriage moves in the proximal direction.

28. The catheter assembly according to claim 27, wherein the flush port and the extension of the housing defines complementary axial guide surfaces to aid limiting the movement of the carriage to movement along the housing axis.

29. The catheter assembly according to claim 1, wherein the housing and the carriage define guide elements to aid limiting the movement of the carriage to movement along the housing axis.

30. The catheter assembly according to claim 29, wherein the guide elements comprise axial guide surfaces formed by an outwardly extending fin of the carriage and an axially extending slot formed in the inner surface of the housing.

31. The catheter assembly according to claim 1, wherein the proximal end of the inner member is secured directly to the proximal end of the handle and the proximal end of the sheath is secured directly to the carriage.

32. The catheter assembly according to claim 1, wherein the carriage driver comprises a tension spring having a proximal end coupled to the proximal end of the housing and a distal end coupled to the carriage so that the tension spring exerts a tension force pulling the carriage in a proximal direction.

33. The catheter assembly according to claim 1, wherein the carriage driver comprises a plurality of nested tension springs each having a proximal end coupled to the proximal end of the housing and a distal end coupled to the carriage so that the tension springs exert a tension force pulling the carriage in a proximal direction.

34. The catheter assembly according to claim 33, wherein adjacent nested tension springs have at least one of: (1) unequal pitches, and (2) opposite directions of wind.

35. The catheter assembly according to claim 1, wherein the carriage driver comprises a spring positioned at least partly within the braking element.

36. The catheter assembly according to claim 1, wherein the carriage driver comprises a compression spring captured between the carriage and the distal end of the housing so that the compression spring exerts a proximally directed force against the carriage.

* * * * *